(12) United States Patent
Lindquist et al.

(10) Patent No.: US 9,248,219 B2
(45) Date of Patent: Feb. 2, 2016

(54) MEDICAL DEVICES HAVING BIOERODABLE LAYERS FOR THE RELEASE OF THERAPEUTIC AGENTS

(75) Inventors: Jeffrey S. Lindquist, Maple Grove, MN (US); Peter G. Edelman, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1488 days.

(21) Appl. No.: 11/900,980

(22) Filed: Sep. 14, 2007

(65) Prior Publication Data

US 2009/0076595 A1    Mar. 19, 2009

(51) Int. Cl.
*A61F 2/06* (2013.01)
*A61L 31/16* (2006.01)
*A61L 31/10* (2006.01)
*A61L 31/14* (2006.01)
*A61L 29/14* (2006.01)
*A61L 27/50* (2006.01)
*A61F 2/30* (2006.01)
*A61L 33/00* (2006.01)

(52) U.S. Cl.
CPC ............... *A61L 31/16* (2013.01); *A61L 31/10* (2013.01); *A61L 31/141* (2013.01); *A61L 31/148* (2013.01); *A61F 2002/30062* (2013.01); *A61L 27/502* (2013.01); *A61L 29/141* (2013.01); *A61L 33/0052* (2013.01); *A61L 2300/604* (2013.01)

(58) Field of Classification Search
CPC . A61L 33/0052; A61L 29/141; A61L 27/502; A61F 2002/30062

USPC .......................................................... 623/1.43
See application file for complete search history.

(56) References Cited

U.S. PATENT DOCUMENTS

| | | | |
|---|---|---|---|
| 5,733,925 A | 3/1998 | Kunz et al. | 514/449 |
| 6,545,097 B2 | 4/2003 | Pinchuk et al. | 525/240 |
| 6,641,611 B2 * | 11/2003 | Jayaraman | 623/1.42 |
| 6,702,850 B1 * | 3/2004 | Byun et al. | 623/1.44 |
| 2002/0065546 A1 * | 5/2002 | Machan et al. | 623/1.13 |
| 2003/0004568 A1 * | 1/2003 | Ken et al. | 623/1.46 |
| 2003/0125803 A1 * | 7/2003 | Vallana et al. | 623/1.42 |
| 2004/0106987 A1 * | 6/2004 | Palasis et al. | 623/1.42 |
| 2004/0143322 A1 * | 7/2004 | Litvack et al. | 623/1.42 |
| 2004/0215336 A1 * | 10/2004 | Udipi et al. | 623/1.42 |
| 2005/0112170 A1 * | 5/2005 | Hossainy et al. | 424/423 |
| 2005/0137678 A1 | 6/2005 | Varma | 623/1.15 |
| 2005/0137684 A1 * | 6/2005 | Changelian et al. | 623/1.42 |

(Continued)

FOREIGN PATENT DOCUMENTS

WO        00/43579        7/2000

OTHER PUBLICATIONS

J. K. Jackson et al. "Characterization of perivascular poly(lactic-co-glycolic acid) films containing paclitaxel", *International Journal of Pharmaceutics*, vol. 283, (2004), pp. 97-109.

(Continued)

*Primary Examiner* — Jacqueline Woznicki
(74) *Attorney, Agent, or Firm* — Seager, Tufte & Wickhem, LLP (57) ABSTRACT

According to an aspect of the present invention, medical devices are provided which comprise: (a) a substrate and (b) bioerodable polymeric layer over the substrate that contains (i) one or more biodegradable polymers, (ii) one or more therapeutic agents, and (iii) one or more plasticizers.

20 Claims, 3 Drawing Sheets

(56) References Cited

U.S. PATENT DOCUMENTS

| | | | | |
|---|---|---|---|---|
| 2006/0041102 | A1* | 2/2006 | Hossainy et al. | 528/354 |
| 2006/0058868 | A1 | 3/2006 | Gale et al. | 623/1.15 |
| 2006/0136051 | A1* | 6/2006 | Furst et al. | 623/1.42 |
| 2006/0171981 | A1 | 8/2006 | Richard et al. | 424/422 |
| 2007/0020312 | A1* | 1/2007 | DesNoyer et al. | 424/426 |
| 2007/0203569 | A1* | 8/2007 | Burgermeister et al. | 623/1.16 |
| 2008/0064841 | A1* | 3/2008 | Hafeli et al. | 528/9 |
| 2008/0132995 | A1* | 6/2008 | Burgermeister et al. | 623/1.15 |

OTHER PUBLICATIONS

L. R. Snyder, "Classification of the Solvent Properties of Common Liquids", *Journal of Chromatographic Science*, vol. 16, (1978), pp. 223-234.

MicroFab: Technology: Research and Development: Biomedical Applications: Stents, downloaded Mar. 23, 2007 from http://www.microfab.com/technology/biomedical/Stents.html, 4pgs.

S. Prabhu et al., "Modeling of degradation and drug release from a biodegradable stent coating", *Journal of Biomedical Materials Research, Part A*, vol. 80, (2006), pp. 732-741.

S. Wood, "Next-generation drug-eluting stents tackle shortcomings of Cypher, Taxus", (Feb. 7, 2006), downloaded Mar. 26, 2007 from http://ww.theheart.org/article/641591.do, 5 Pages.

J. C. Middleton et al., "Synthesis Biodegradable Polymers as Medical Devices", *Medical Plastics and Biomaterials Magazine*, (MPB Archives) Mar. 1998, 9 Pages.

F. Pivert, Terumo Europe N.V. Press Release, "Terumo Europe N.V. Enrols First Patient in Clinical Trial of the Nobori™ Drug-eluting Coronary Stent", (May 26, 2007), downloaded on Mar. 26, 2007 from http://www.terumo-europe.com/_press_releases/may_26_2005.html, 1 Page.

\* cited by examiner

MEDICAL DEVICES HAVING BIOERODABLE LAYERS FOR THE RELEASE OF THERAPEUTIC AGENTS

FIELD OF THE INVENTION

The present invention relates to medical devices which are a least partially bioerodable and which release therapeutic agents.

BACKGROUND

Numerous polymer-based medical devices have been developed for implantation or insertion into the body. For example, in recent years, drug eluting coronary stents, which are commercially available from Boston Scientific Corp. (TAXUS and PROMUS), Johnson & Johnson (CYPHER) and others, have become the standard of care for maintaining vessel patency. These existing products are based on metallic balloon expandable stents with biostable polymer coatings, which release antiproliferative drugs at a controlled rate and total dose.

Figure 1:
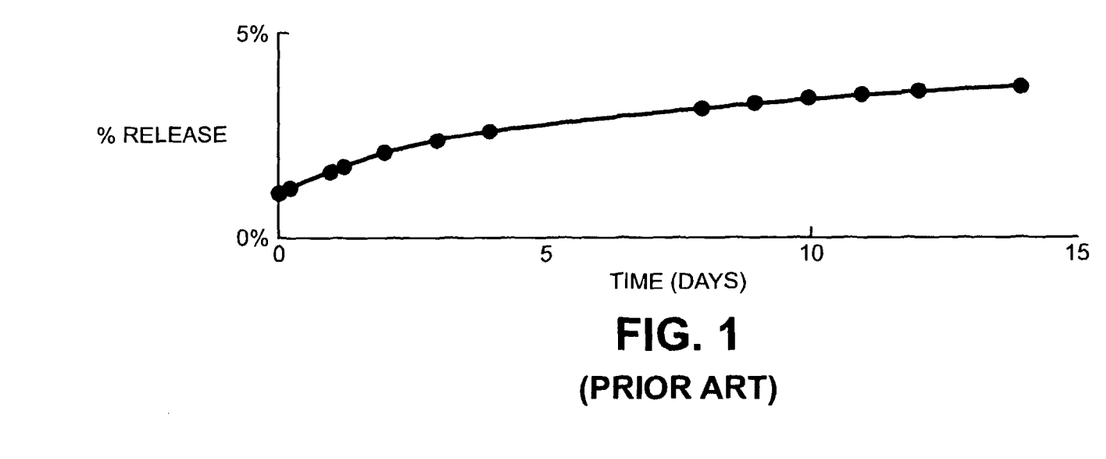
FIG. 1 is a plot of percent paclicaxel release as a function of time from a stent coating that contains 25 wt % paclitaxel and 75 wt % SIBS, in accordance with Pub. No. US 2006/0171981 to Richard et al.

Specific examples of biostable polymers for biostable drug eluting polymer coatings include homopolymers and copolymers, such as poly(ethylene-co-vinyl acetate), poly(vinylidene fluoride-co-hexafluoropropylene) and poly(isobutylene-co-styrene), for example, poly(styrene-b-isobutylene-b-styrene triblock copolymers (SIBS), which are described in U.S. Pat. No. 6,545,097 to Pinchuk et al. FIG. 1, which is taken from Pub. No. US 2006/0171981 to Richard et al., illustrates a release profile of a stent coating that contains 25 wt % paclitaxel and 75 wt % SIBS.

Biodegradable polymers may have certain advantages over biostable polymers. For example, because they erode over time, biodegradable polymers may reduce or eliminate long term effects that may be associated with non-biodegradable polymers (e.g., foreign body effects, late stent thrombosis, etc.).

SUMMARY OF THE INVENTION

According to an aspect of the present invention, medical devices are provided which comprise: (a) a substrate and (b) bioerodable polymeric layer over all or a portion of the substrate that contains (i) one or more biodegradable polymers, (ii) one or more therapeutic agents, and (iii) one or more plasticizers.

Advantages of the present invention, in addition to those advantages associated with biodegradable polymers that are described above, include enhanced ability to modulate/influence one or more of the following: a) therapeutic agent release behavior of the bioerodable layer, b) rate of bioerosion of the bioerodable layer, and/or c) mechanical properties of the bioerodable layer.

Other aspects and embodiments of the invention, as well as various additional advantages of the same, will become readily apparent to those of ordinary skill in the art upon reading the disclosure to follow.

DETAILED DESCRIPTION OF THE INVENTION

According to an aspect of the present invention, medical devices are provided which comprise: (a) a substrate and (b) bioerodable polymeric layer over all or a portion of the substrate that contains (i) one or more (i.e., blends of) biodegradable polymers, (ii) one or more therapeutic agents, and (iii) one or more plasticizers.

As discussed further below, in certain embodiments of the invention, a further bioerodable polymeric layer is provided, which contains one or more biodegradable polymers and one or more therapeutic agents, and which may or may not contain one or more plasticizers. The bioerodable polymeric layers may be provided, for example, over, under, or lateral to one another.

In certain embodiments of the invention, polymeric layers for use in the medical devices of the invention may contain, for example, (a) from 50 wt % or less to 60 wt % to 70 wt % to 80 wt % to 90 wt % to 95 wt % to 97.5 wt % to 99 wt % or more of one or more types of biodegradable polymers, (b) from 1 wt % or less to 2.5 wt % to 5 wt % to 10 wt % to 20 wt % to 30 wt % or more of one or more types of therapeutic agent and (c) from 0 wt % to 1 wt % to 2.5 wt % to 5 wt % to 10 wt % to 20 wt % to 30 wt % to 40 wt % to 50 wt % or more of one or more types of plasticizers.

"Therapeutic agents," "drugs," "pharmaceutically active agents," "biologically active materials," and other related terms may be used interchangeably in the present disclosure.

As used herein a "layer" of a given material is a region of that material whose thickness is small compared to both its length and width. A layer need not be planar, for example, taking on the contours of an underlying substrate. Layers in accordance with the present invention may be disposed over all or a portion on an underlying substrate and can be discontinuous (e.g., patterned). Terms such as "film," "layer" and "coating" may be used interchangeably herein.

As used herein, a "polymeric layer" is one that contains one or more types of polymers (i.e., a single type of polymer of a mixture of polymers). As is well known, "polymers" are molecules that contain multiple copies (e.g., 2 to 5 to 10 to 25 to 50 to 100 to 250 to 500 to 1000 to 10,000 or more copies) of one or more constitutional units, commonly referred to as monomers. As used herein, the term "monomers" may refer to the free monomers and those that are incorporated into polymers, with the distinction being clear from the context in which the term is used. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), and dendritic configurations (e.g., arborescent and hyperbranched polymers), among others. Depending on the polymer structure, the polymer may contain amorphous regions or a mixture of amorphous and crystalline regions (known as semicrystalline). As used herein, "homopolymers" are polymers that contain multiple copies of a single type of monomer. "Copolymers" are polymers that contain multiple copies of at least two different monomers, examples of which include random, statistical, gradient, periodic (e.g., alternating), and block copolymers.

As used herein, a polymer is "biodegradable" if it undergoes bond cleavage along the polymer backbone in vivo, regardless of the mechanism of bond cleavage (e.g., enzymatic breakdown, hydrolysis, oxidation, etc.).

As used herein, a polymer is "biostable" if it does not undergo substantial bond cleavage along the polymer backbone in vivo.

"Bioerosion" or "bioabsorption" of a polymeric component (e.g., a polymeric layer) of a medical device is defined herein to be a result of polymer biodegradation (as well as other in vivo disintegration processes such as dissolution, etc.) and is characterized by a substantial loss in vivo over time (e.g., the period that the device is designed to reside in a patient) of the original polymer mass of the polymeric component. "Biostablity" of a polymeric component, on the other hand, is characterized herein by the substantial maintenance in vivo over time of the original polymer mass of the polymeric component. The polymer layers of the invention are adapted to be substantially completely bioeroded (i.e., 95 wt % to 97.5 wt % to 99 wt % to 100 wt % of the polymer mass of each layer bioerodes) in vivo over the period that the device is designed to reside in a patient.

As used herein a "plasticizer" is a substance that, when added to a polymeric component, changes the polymer one or more ways relative to the same polymeric component without the plasticizer. The most commonly measured effect of a plasticizer is a lowering in the glass transition (Tg) of a polymer as measured by Differential Scanning Calorimetry (DSC) or a change mechanical properties such as the tan delta. For a device coated with a polymeric coating layer containing a therapeutic agent, other beneficial effects that may be imparted to the coating include modulation of the drug release rate and improved coating mechanical properties.

Examples of medical devices benefiting from the present invention vary widely and include implantable or insertable medical devices from which one or more therapeutic agents may be delivered, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, or other devices that are implanted or inserted into the body and from which therapeutic agent is released.

The medical devices of the present invention thus include, for example, implantable and insertable medical devices that are used for systemic diagnosis and treatment, as well as those that are used for the localized diagnosis and treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

Examples of biodegradable polymers for use in the polymeric layers of present invention may be selected from one or more (i.e., mixtures) suitable members of the following, among many others: (a) polyester homopolymers and copolymers such as polyglycolic acid (PGA), polylactic acid (PLA) including poly-L-lactic acid, poly-D-lactic acid and poly-D, L-lactic acid, poly(beta-hydroxybutyrate), polygluconate including poly-D-gluconate, poly-L-gluconate, poly-D,L-gluconate, poly(epsilon-caprolactone), poly(delta-valerolactone), poly(p-dioxanone), poly(lactic acid-co-glycolic acid) (PLGA) which can have a range of ratios of lactic acid to glycolic acid, additionally with either the racemic or meso DL lactide or the pure L-lactide, poly(lactic acid-co-delta-valerolactone), poly(lactic acid-co-epsilon-caprolactone), poly (lactic acid-co-beta-malic acid), poly(beta-hydroxybutyrate-co-beta-hydroxyvalerate), poly[1,3-bis(p-carboxyphenoxy) propane-co-sebacic acid], and poly(sebacic acid-co-fumaric acid), among others, (b) poly(ortho ester) homopolymers and copolymers such as those synthesized by copolymerization of various diketene acetals and diols, among others, (c) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others; (d) polycarbonate homopolymers and copolymers such as poly(trimethylene carbonate), poly (lactic acid-co-trimethylene carbonate) and poly(glycolic acid-co-trimethylene carbonate), among others, and (e) amino-acid-based polymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

Where one or more types of poly(lactic acid-co-glycolic acid) (PLGA) are employed in the layers of the invention, whether the lactic acid is D-lactic acid, L-lactic acid or a mixture of D- and L-lactic acid, the mol % of lactic acid in PLGA for either the inner or the outer layer may range from 1 to 99 mol %, for example, ranging from 30 mol % or less to 40 mol % to 50 mol % to 75 mol % to 85 mol % to 90 mol % or more.

In many embodiments, the one or more types of biodegradable polymers will have a number average molecular weight of 10,000 or more, for example, ranging from 10,000 to 25,000 to 50,000 to 75,000 to 100,000 to 125,000 to 150,000 or more.

As noted above, in addition to one or more biodegradable polymers and one or more therapeutic agents, bioerodable layers within the medical devices of the invention may also contain one or more plasticizers in some embodiments. Without wishing to be bound by theory, it is believed plasticizers act to increase polymer chain mobility and free volume, improving the mechanical properties of the polymeric layers such as flexibility. Moreover, as discussed elsewhere herein, the addition of plasticizers can also modulate the therapeutic agent release properties of the polymeric layers and the biodegradation rate of the polymeric layers, among other possible effects.

Examples of plasticizers for bioerodable layers in accordance with the present invention include those that contain or consist of the monomers making up the biodegradable polymer(s) within the bioerodable layer, and they include the monomers themselves as well as oligomers of the same (i.e., defined herein as polymers ranging from 2 to 3 to 5 to 10 units in length), and short polymers of the same (i.e., defined herein as polymers of 11 or more monomer units in length up to a molecular weight of 10,000) For example, in some embodiments, the plasticizers will have a number average molecular weight ranging from 500 to 1,000 to 2,500 to 5,000 to 7,500 to 10,000. Plasticizers therefore include monomers, oligomers, and short polymers of the following: glycolic acid, lactic acid (D-, L- or combinations), gluconic acid (D-, L- or combinations), beta-hydroxybutyric acid, beta-hydroxyvaleric acid, malic acid, epsilon-caprolactone, delta-valerolactone, as well as various other C2-C15 hydroxy acids and C3-C15 cyclic esters; adipic acid, adipic anhydride, suberic acid, suberic anhydride, sebacic acid, sebacic anhydride, dodecanedioic acid, dodecanedioic anhydride, and other C2-C15 diacids and C3-C15 cyclic anhydrides; 1,3-Dioxan-2-one and other C3-C15 cyclic carbonates, among many others.

For instance, where PLGA is selected as a polymer for use in a bioerodable layer in accordance with the invention, the plasticizer may be based on lactic acid, glycolic acid or both. Lactic acid and glycolic acid are the natural degradation products of PLGA and are biocompatible since they are found in the body as metabolites and are part of the Krebs cycle. Examples of such plasticizers include one or more of the following: glycolic acid, glycolic acid dimer, glycolic acid trimer, further glycolic acid oligomers and short polymers, lactic acid, lactic acid dimer, lactic acid trimer, further lactic acid oligomers and short polymer, glycolic acid-lactic acid dimer and other glycolic acid-lactic acid oligomers and short polymers, wherein the forgoing oligomers and short polymers may be linear or cyclic in configuration. As elsewhere herein the lactic acid may be L-lactic acid, D-lactic acid or a mixture of the same, where the relative amounts of the L- and D-isomers can be measured using specific rotation. Various species, including inherent short polymers, oligomers or unreacted monomers may be distinguished using several techniques such as gel permeation chromatography (e.g., with columns that resolve the low molecular weight of the distribution), end group analysis using NMR, and titration, among others.

In some embodiments, the weight ratio of the one or more biodegradable polymers to the one or more plasticizers in the polymeric layers ranges from 10:1 to 100:1 to 1000:1 to 10000:1.

In some embodiments, an analysis of the molecular weight of the polymeric species within a polymeric layer in accordance with the invention may be multimodal, for example, having one mode corresponding to a small polymer plasticizer and another mode corresponding to a biodegradable polymer.

As noted above, in some embodiments, plasticizers for bioerodable layers in accordance with the present invention include those that contain or consist of the monomers making up the biodegradable polymer(s) within the bioerodable layer. In some embodiments, the plasticizers may correspond to monomers, oligomers and small polymers that comprise or consist of monomers that do not correspond to those making up the one or more types of biodegradable polymers within the bioerodable layers. Such plasticizers may be water soluble or insoluble. If the plasticizing molecule is not water soluble, it may biodegrade to water soluble fragments. Such plasticizers may or may not be miscible with one or more biodegradable polymers within the bioerodable layer or immiscible.

For example, where PLGA is selected as a polymer, examples of suitable miscible plasticizing polymers include methoxypolyethylene glycol (MePEG) and polylactic acid-MePEG diblock copolymer (PLA-MePEG), both of which are water soluble. These polymers are known to plasticize PLGA polymers (50:50 and 85:15), increasing their elasticity. These polymers have also been observed to reduce the glass transition temperature (Tg) of PLGA polymers, thereby making otherwise brittle PLGA flexible at room temperature. Single Tg values intermediate between the Tg values of the pure components have been observed for blends containing PLGA and the above plasticizing polymers, which is indicative of the miscibility of the components. MePEG was observed to partition out of the PLGA films in aqueous media over a period of 72 hours, with an accompanying increase in Tg. A benefit of this behavior is that a polymeric material (e.g., a stent coating) is plasticized during implantation or insertion (e.g., during stent expansion in a lesion to create intimate contact between the abluminal surface of the stent and the artery wall). After placement, when flexibility and durability are no longer needed, the plasticizer elutes from the polymeric material. This may improve mechanical properties and, where a therapeutic agent is present, shift the release profile of the therapeutic agent to a desired range. The PLA-MePEG on the other hand showed controlled release over a period of about 1 month, which was attributed to affinity of the polylactic acid blocks of the PLA-MePEG with the PLGA. Addition of paclitaxel was observed to offset somewhat the increase in elasticity arising from the plasticizing polymers (paclitaxel has also been observed to increase the Tg of PLA). Paclitaxel was observed to be in the form of a particulate dispersion. Paclitaxel release from PLGA-MePEG films was found to be very slow (less than 5% after 16 days), but was reported to be dramatically increased for PLGA films containing 30 wt % PLA-MePEG diblock copolymer (approx. 15% after 10 days). It was speculated that this could represent a critical loading level, causing a significantly increase in matrix hydrophilicity and leading to increased water uptake, the formation of water-filled channels in the matrix, and greatly increased paclitaxel release rates. For further information, see, e.g., J. K. Jackson et al., *Int. J. Pharm.* 283 (2004) 97-109.

Adding one or more plasticizers to polymeric layers in accordance with the invention will, of course, provide a plasticizing action as discussed above. This can improve the mechanical properties of the polymeric layer, for instance, resulting in one or more of the following, among others: increased resistance to cracking/crazing propagation, improved bending/modulus properties, increased fatigue resistance, and resistance to particulate formation in vivo, both acute and chronic, among other properties.

Adding one or more of the plasticizers can also affect the bioerosion rate of the polymeric layer, for example, increasing the same. For example, a plasticizer may partition out of the polymeric layer in vivo, increasing void volume, creating a porous structure (particularly in the case of partially phase-separated immiscible plasticizers), and promoting the transport of water into the layer. As another example, certain plasticizers may act as catalysts for the biodegradation process. For example, glycolic acid and lactic are known to increase the degradation rate of PLGA due to a local lowering of the pH. Where a therapeutic agent is present, adding one or more of plasticizers can affect the rate of therapeutic agent release from the polymeric layer. In addition to affecting release by affecting the degradation rate of the polymer, plasticizer addition may also have one or more of the following effects, each of which may influence therapeutic agent release: the plasticizer may act to lower the Tg of the polymer, the plasticizer may create a phase-separated matrix for the therapeutic agent which can, for example, lead to void formation (e.g., where the plasticizer is immiscible), the plasticizer may solubilize the therapeutic agent of interest which may, for example, lead to more rapid diffusion from the polymer matrix, and/or the plasticizer may drive drug to the surface based compatibility with certain species in the polymeric layer. With respect to solubilization of the therapeutic agent, more hydrophilic plasticizers may be selected to dissolve more hydrophilic therapeutic agents, more hydrophobic plasticizers may be selected to dissolve more hydrophobic therapeutic agents, and so forth. As a specific example, where PLGA is selected for use as the biodegradable polymer, one may wish to select a lactic-acid-based plasticizer for more a more hydrophobic therapeutic agent (e.g., paclitaxel) and a glycolic-acid-based plasticizer for a more hydrophilic therapeutic agent (e.g., everolimus).

Figure 2A:
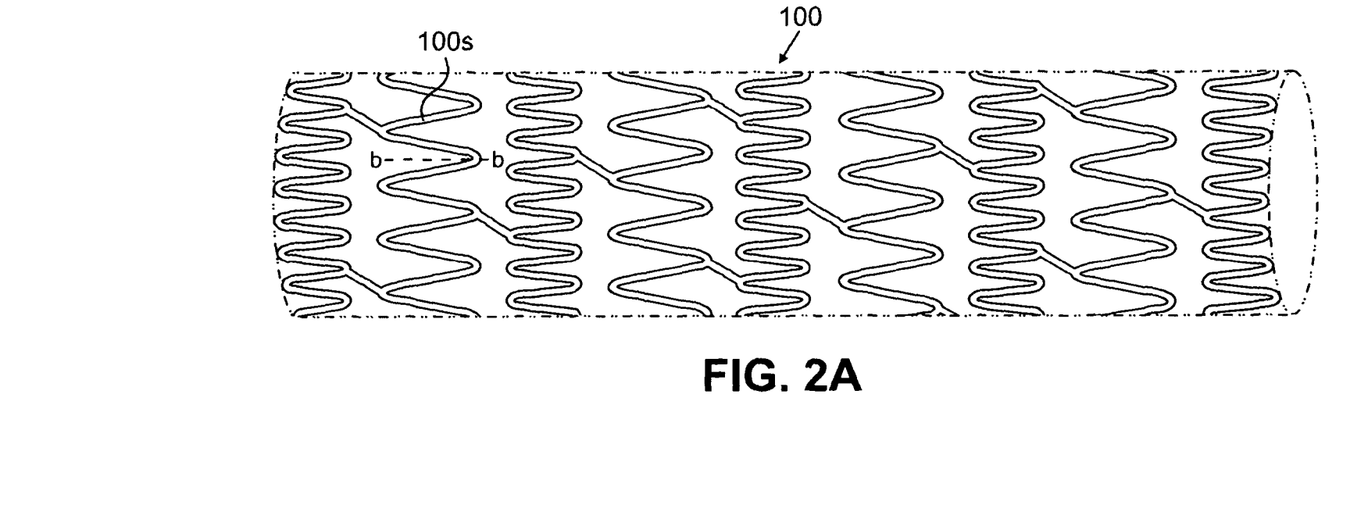
FIG. 2A is a schematic perspective view of a coronary stent, in accordance with an embodiment of the invention.
Figure 2B:
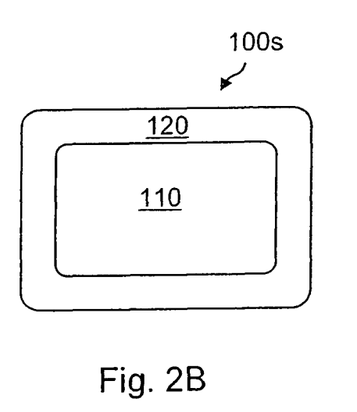
FIG. 2B is a schematic cross-sectional view taken along line b-b of FIG. 2A.
Figure 3:
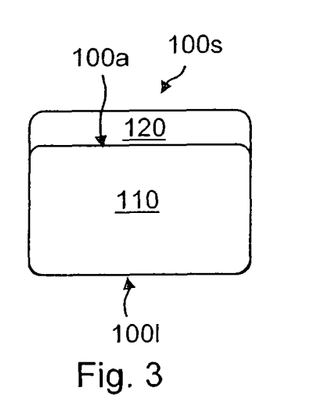
FIGS. 3 and 4A-4B are further schematic cross-sectional views of stent struts, in accordance with various embodiments of the invention.

A stent in accordance with the present invention will now be described with reference to the drawings. In this regard, FIG. 2A is a schematic perspective view of a stent 100 which contains a number of interconnected struts 100s. FIG. 2B is a schematic cross-section taken along line b-b of the strut 100s of FIG. 2. The stent strut 100s shown includes a stent substrate 110 and a bioerodable polymeric layer 120 in accordance with the present invention. An alternative embodiment is illustrated in FIG. 3, which, like FIG. 2B, is a schematic cross-sectional view of a stent strut. In FIG. 3, however, the polymeric layer 120 covers the abluminal surface 10a of the stent substrate 110, but not the opposing luminal surface 100l or the intervening side surfaces. In the embodiments of FIGS. 2B and 3, the bioerodable polymeric layer 120 contains one or more biodegradable polymers (i.e., a single type of biodegradable polymer or a mixture of two or more types of biodegradable polymers), one or more therapeutic agents (i.e., a single type of therapeutic agent or a mixture of two or more types of therapeutic agents), and one or more plasticizers (i.e., a single type of plasticizer or a mixture of two or more types of plasticizer) as described above.

Figure 4A:
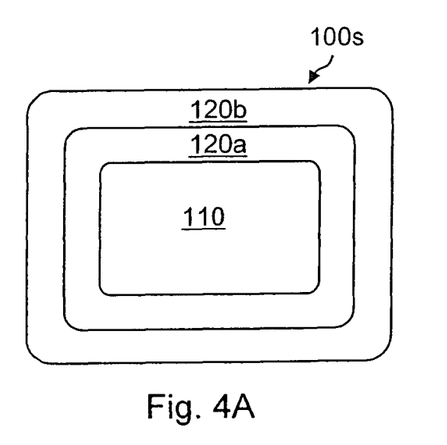
Figure 4B:
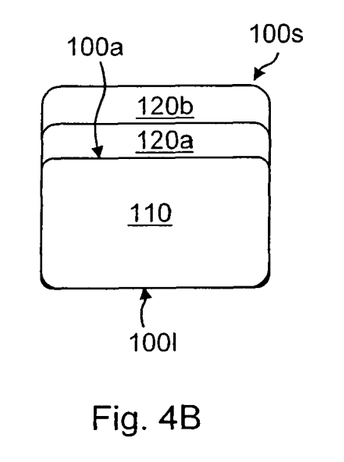

In accordance with a further embodiment of the invention, FIG. 4A, like FIGS. 2B and 3, is a schematic cross-sectional view of a stent strut 100s. However, the stent strut 100s shown in FIG. 4A includes a stent substrate 110 an inner bioerodable polymeric layer 120a and an outer bioerodable polymeric layer 120b, in accordance with an embodiment of the invention. An alternative embodiment is illustrated in FIG. 4B, which, like FIG. 4A, is a schematic cross-sectional view of a stent strut 100s and includes a stent substrate 110 and inner and outer bioerodable polymeric layers 120a, 120b. In FIG. 4B, however, the inner and outer bioerodable polymeric layers 120a, 120b are disposed over the abluminal surface 110a of the stent substrate 110, but not the opposing luminal surface 100l or the intervening side surfaces. Each of the inner and outer bioerodable polymeric layers 120a, 120b in FIGS. 4A and 4B contains one or more biodegradable polymers (i.e., a single type of biodegradable polymer or a mixture of two or more types of biodegradable polymers) and one or more therapeutic agents (i.e., a single type of therapeutic agent or a mixture of two or more types of therapeutic agents). Moreover, one or both of the inner and outer bioerodable polymeric layers 120a, 120b contains one or more plasticizers (i.e., a single type of plasticizer or a mixture of two or more types of plasticizer) as described above.

By "inner" is merely meant that the bioerodable polymeric layer is inner relative to the outer bioerodable polymeric layer—not that it is necessarily the innermost layer of the device, although it can be. Similarly, by "outer" is meant that the bioerodable polymeric layer is outer relative to the inner bioerodable polymeric layer—not that it is necessarily the outermost layer of the device, although it can be.

As discussed above, FIG. 1 is a release profile for a hydrophobic drug (paclitaxel) from a biostable polymeric layer. Biodegradable polymer layers, on the other hand, typically do not yield release profiles like those shown in FIG. 1. By way of background and without wishing to be bound by theory, the release of a drug from a thin biodegradable polymeric film typically consists of three phases. The first phase is an initial burst phase (e.g., at days 0-10), which is due to dissolution of drug residing on the surface of the coating. The rate of release during this first phase may be dictated, for example, by the solubility and rate of dissolution of the drug (e.g., drug particles) into the surrounding media. The second phase is characterized by a slower sustained release phase. The sustained release phase is governed by diffusion processes, including the rate of diffusion of the drug through the polymer matrix (which is a function of drug solubility in the polymer, among other factors). Because the layer is bioerodable, however, a third phase commonly ensues in which an increase in drug release is observed, which is influenced by the hydrolysis behavior of the polymer as it bioerodes. Eventually, drug release ceases due to the complete degradation of the polymeric film. For a more complete discussion of the factors that affect the polymer degradation rate, see, e.g., S. Prabhu et al., "Modeling of degradation and drug release from a biodegradable stent coating", *Journal of Biomedical Materials Research, Part A,* 80 (2007) 732-741.

Figure 5:
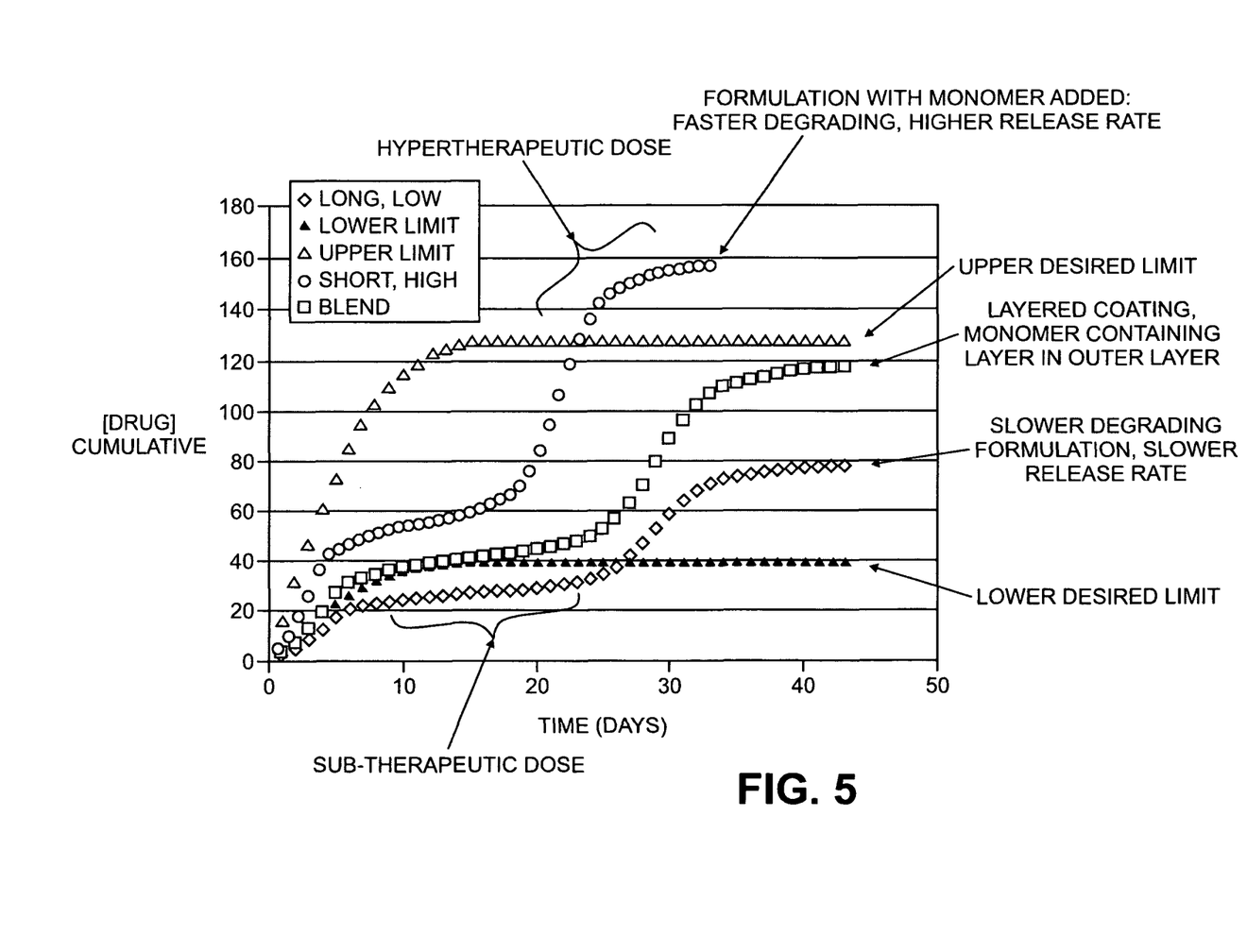
FIG. 5 illustrates various hypothetical release profiles.

For example, FIG. 5 is a graphical representation of a few hypothetical cumulative release curves for release of a hydrophobic drug (e.g., paclitaxel, among many others) from single- and double-layer release systems that further contain a biodegradable polyester (e.g., PLGA). FIG. 5 contains lower (dark triangles) and upper (light triangles) hypothetical cumulative release target curves between which it is desired to maintain cumulative drug release.

FIG. 5 further includes a curve (diamonds) representing hypothetical cumulative release from a slower degrading formulation (e.g., one containing PLGA with an 85:15 wt/wt lactic acid:glycolic acid ratio). For example, the coating may correspond to an abluminal stent coating (e.g., 100 microgram weight) which contains 85-90 wt % 85:15 PLGA having a molecular weight of ~50-60 kDa and about 10-15 wt % paclitaxel. Consistent with the description in the prior paragraph, this curve shows an initial burst, followed by a slower sustained release phase, followed by an increase in release, which eventually tapers off. As seen from FIG. 5, the initial burst for this curve is insufficient to surpass the lower cumulative release target, and a sub-therapeutic dose is released in the early stages.

The curve designated by circles in FIG. 5 represents cumulative release from a faster degrading formula (e.g., one containing PLGA with a 50:50 wt/wt lactic acid:glycolic acid ratio or one containing PLGA with an 85:15 wt/wt lactic acid:glycolic acid ratio and an added plasticizer, such as a monomer, which in this particular hypothetical instance is provided at a level such that the release that is observed during polymer degradation exceeds the desired upper limit). For example, the coating may correspond to an abluminal stent coating (e.g., 200 microgram weight) which contains 85-90 wt % 50:50 PLGA having a molecular weight of ~50-60 kDa and about 10-15 wt % paclitaxel. Like the prior formulation (designated by diamonds), this curve shows an initial burst, followed by a slower sustained release phase, followed by an increase in release that eventually tapers off, although these events happen at an earlier time. Because the formula contains twice the amount of drug as the prior formulation, the initial burst is sufficient surpass the lower limit. However, the subsequent increase in release that is observed during polymer degradation exceeds the desired upper limit, leading to a hyper-therapeutic cumulative dose.

The hypothetical curve represented by squares in FIG. 5 is for a two layer composition, representing a blend of two single layer schemes. The first (underlying) layer is like that described above for a slower degrading formula (e.g., one containing paclitaxel and PLGA with an 85:15 wt/wt lactic acid:glycolic acid ratio). Disposed over this layer is layer that contains plasticizer in addition to paclitaxel and PLGA with a 85:15 lactic acid:glycolic acid wt/wt ratio. As a specific example, the abluminal surface of a stent may be first coated with 100 micrograms of a first layer based on 85:15 PLGA having a molecular weight of ~60 kDa, which contains about 10 wt % paclitaxel (PTx). This layer is then overcoated with 30 micrograms of a second layer based on 85:15 PLGA having a molecular weight of ~60 kDa, which contains about 10 wt % PTx and about 10% lactic acid as a monomeric plasticizer.

Thus, the present invention provides an approach whereby plasticizers are used to modulate drug release rate and bioerosion behavior for coatings that utilize existing 50/50, 75/25, or 85/15 composition ratio PLGA materials and mixtures thereof, among many others, while at the same time providing improved acute and chronic mechanical behavior (including resistance to cracking/crazing, bending modulus properties, fatigue resistance, and resistance to particulate formation). As a specific example, by adding one or more types of plasticizer to 85/15 PLGA material, it may be possible to increase the amount of drug released in the initial release phase (e.g., increasing drug release from sub-therapeutic to therapeutic levels) and to modulate the bioerosion rate (e.g., decreasing the time required for bioerosion and thus the time period where one is vulnerable to foreign body effects). Moreover, 85/15 PLGA is normally a brittle material, which may lead to problems under certain circumstances (e.g., coating cracking upon stent expansion); however, the addition of one or more types of plasticizer will improve the flexibility of the polymer. Thus, the present invention may provide those of ordinary skill in the art with the ability to tailor the mechanical properties, drug release rate and the degradation rate in a synergistic way by adding controlled amounts of one or more types of plasticizer (e.g., monomers, oligomers and small polymers based on lactic acid, glycolic acid or both) to PLGA polymers of different LA/GA ratios and mixtures thereof.

As suggested from the above discussion, the present invention provides various ways of affecting the mechanical, release and bioerosion characteristics of a given drug-containing layer. These include, for example, the nature of the coating (e.g., single layer or multilayer structure) selected, the coating weight selected, and the relative amounts of the various coating constituents selected, including the one or more types of biodegradable polymer, one or more types of plasticizer and one or more types of therapeutic agent within the layer.

With respect to the one or more types of plasticizer, monomeric, oligomeric and/or short polymeric plasticizers of varying hydrophilicity/hydrophobicity may be employed.

The specific biodegradable polymer(s) employed is also important. For example, the monomer content will have a significant effect upon the mechanical biodegradation and release characteristics. For instance, polymers having relatively high rates of hydrolysis, such as polyanhydrides and polyorthoesters, may be used to promote more rapid release, whereas polymers having relatively lower rates of hydrolysis, such as polyesters, may be used to promote more prolonged release. Moreover, different monomers within a given class of monomers may be employed to alter release. For example, PLA erodes slower than PGA. Similarly, for copolymers of lactic acid and glycolic acid (PLGA), higher amounts of lactic acid lead to slower rates of erosion. These effects are thought to be due to the fact that lactic acid is more hydrophobic than glycolic acid.

Polymer molecular weight is also known to affect release. For instance, polymers having higher molecular weight may be selected for extended release applications as these tend to biodegrade at a lower rate than polymers having lower molecular weight, and vice versa.

Moreover, layers may be formed in which the plasticizer is preferentially located at the surface of the layer (which may or may not be covered by another layer), either during layer formation or post-layer-formation processing, which will result in desirable self-stratification (i.e., concentration gradient that is a function of depth). An advantage of having a plasticizer-rich surface is that a layer may be formed which contributes to a desired burst characteristic, for example, in a layer containing PLGA of high molecular weight (e.g., number average mol. wt. of 50,000 to 70,000 or more) and high lactide content (e.g., 85/15). As used herein a surface is "plasticizer-rich" where the plasticizer concentration at the surface of the layer is at least 50% higher than the overall plasticizer concentration in the layer, and may be measured, for example, by one or more of the following: atomic force microscopy, confocal Raman spectroscopy or time-of-flight secondary ion mass spectrometry.

For example, a plasticizer-rich surface may be created by solvent vapor exposure or by providing a solvent which has a greater affinity for the base polymer than the plasticizer, thereby urging the plasticizer to the polymer surface (rather than the bulk). One way of selecting a solvent composition that has greater affinity for the base polymer relative to the plasticizer is to select a solvent whose polarity more closely matches that of the base polymer. One measure of the polarity of solvents is known as the Snyder Polarity Index (PI). See Snyder, L. J., "Classification of the Solvent Properties of Common Liquids," *Chromatography*, 92, 1974, 223-230. In general, the affinity of the solvent for each of the components (base polymer, therapeutic agent and plasticizer) is such that the solvent is able to dissolve the components to create a solution suitable for forming a polymeric coating layer. However, as noted above, the solvent selected should nonetheless have a higher affinity for the base polymer and than the plasticizer, where one wishes to urge the plasticizer to the polymer surface.

A plasticizer-rich surface may also be created by application of one or more plasticizers (as well as other agents, if desired, such as one or more therapeutic agents, etc.) to the surface of a bioerodable polymeric layer that contains one or more biodegradable polymers (as well as other agents, if desired, such as one or more therapeutic agents, one or more plasticizers, etc.).

As noted above, "therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, and (ee) thymosin beta 4 (ff) phospholipids including phosphorylcholine, phosphatidylinositol and phosphatidylcholine, (gg) VLA-4 antagonists and VCAM-1 antagonists.

Specific examples of non-genetic therapeutic agents include taxanes such as paclitaxel, (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Further additional therapeutic agents useful for the practice of the present invention are also disclosed in U.S. Pat. No. 5,733,925 to Kunz.

A variety of materials may be used as substrate materials for the medical devices of the present invention. Examples of such materials include non-metallic materials such as ceramics, homopolymers, copolymers, and polymer blends. Examples of such materials also include metallic materials, which may be selected, for example, from metals such as gold, iron, niobium, platinum, palladium, iridium, osmium, rhodium, titanium, tantalum, tungsten, ruthenium, magnesium, iron and zinc, among others, and metal alloys such as those comprising iron and chromium (e.g., stainless steels, including platinum-enriched radiopaque stainless steel), niobium alloys, titanium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (and their alloys with combinations of Ce, Ca, Zn, Zr and Li), among others. Composites of two or more of the forgoing (e.g., polymer-ceramic composites, polymer-metal composites, metal-ceramic composites, etc.) may also be employed. Materials having both super elastic and shape-memory characteristics, for example, alloys comprising nickel and titanium (e.g., Nitinol), may be beneficial in certain embodiments.

Numerous techniques are available for forming the medical devices (or portions thereof) of the invention.

For example, in some embodiments, solvent-based techniques are used to form one or more of the polymeric layers in accordance with the present invention. Using these techniques, layers can be formed by first providing a solution that contains the chemical species that make up the layer (e.g., polymer, plasticizer, therapeutic agent, and/or other chemical species), dissolved or dispersed in a solvent system, and subsequently removing the solvent system. The solvent system that is ultimately selected will contain one or more solvent species, which may be selected based on their ability to dissolve or disperse the various chemical species, as well as other factors, including drying rate, surface tension, etc. Examples of solvent-based techniques include spin coating techniques, web coating techniques, coating via an applicator (e.g., roller, brush, ink jet techniques, etc.), solvent spraying techniques, dipping techniques, techniques involving coating via mechanical suspension including air suspension, electrostatic techniques, and combinations of these processes, among others.

In other embodiments, thermoplastic processing techniques are used to form one or more polymeric layers in accordance with the present invention. Using these techniques, layers can be formed by first providing a melt that contains the chemical species that make up the polymeric layer, and subsequently cooling the melt. Examples of thermoplastic techniques include dipping, spraying, spin coating, web coating, extrusion, coating via an applicator (e.g., roller, brush, ink jet, etc.), and combinations of these processes, among others.

Other ways of forming medical devices in accordance with the present invention will become readily apparent to those of ordinary skill upon review of the above description of the invention.

EXAMPLES

Example 1

A 16 mm Liberte WH stent (Boston Scientific, Natick, Mass., USA) is provided with two abluminal layers. The inner layer is a 100 μg layer that consists of about 90 wt % 85:15 PLGA having a molecular weight of ~60 kDa and about 10 wt % PTx. The outer layer is a 30 μg layer that consists of about 80 wt % 85:15 PLGA having a molecular weight of ~60 kDa, about 10 wt % paclitaxel, and about 10% lactic acid as a monomeric plasticizer.

Example 2

A 20 mm Liberté stent (Boston Scientific, Natick, Mass., USA) is provided with a single layer that consists of a blend of 7525 DLG 1A from Lakeshore Biomaterials, Birmingham, Ala., USA (75:25 PLGA having acid end groups and an inherent viscosity of 0.05-0.15 dL/g, which is a short polymer having a molecular weight on the order of 10,000 Daltons) and 7525 DLG 4A from Lakeshore Biomaterials (75:25 PLGA having acid end groups, an inherent viscosity of 0.35-0.55 dL/g and a molecular weight on the order of 50,000 to 70,000 Daltons) at a ratio of 25:75 w:w 7525 DLG 1A:7525 DLG 4A, at 5% paclitaxel and 125 microgram coat weight.

Example 3

A 20 mm Liberté stent (Boston Scientific, Natick, Mass., USA) is provided with 2 abluminal layers that consists of the following (a) 8515 DLG 1A from Lakeshore Biomaterials (85:15 PLGA having acid end groups and an inherent viscosity of 0.05-0.15 dL/g, which is a short polymer having a molecular weight on the order of 10,000 Daltons) at 2.75% paclitaxel and 100 microgram coat weight over (b) 8515 DLG 4A from Lakeshore Biomaterials (85:15 PLGA having acid end groups, an inherent viscosity of 0.35-0.55 dL/g and a molecular weight on the order of 50,000 to 70,000 Daltons) at 2.75% paclitaxel and 150 microgram coat weight.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising (a) a substrate and (b) a bioerodable polymeric layer over the substrate that comprises (i) 50 wt % to 99 wt % of a biodegradable polymer selected from poly(lactic acid) and poly(lactic acid-co-glycolic acid), said biodegradable polymer having a number average molecular weight of 10,000 or more, (ii) a therapeutic agent, and (iii) 1 wt % to 50 wt % of a plasticizer selected from glycolic acid, an oligomer comprising glycolic acid, and combinations thereof.

2. The medical device of claim 1, wherein the medical device is a vascular medical device.

3. The medical device of claim 1, wherein the substrate is a metallic stent or a biodegradable polymeric stent.

4. The medical device of claim 1, wherein the therapeutic agent is selected from antiproliferative agents, anti-thrombotic agents, anti-angiogenic agents, anti-restenotic agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

5. The medical device of claim 1, wherein the poly(lactic acid-co-glycolic acid) comprises 30 to 100 wt % lactic acid and 0 to 70 wt % glycolic acid.

6. The medical device of claim 1, wherein the bioerodable polymeric layer comprises said glycolic acid as said plasticizer.

7. The medical device of claim 1, wherein the bioerodable polymeric layer comprises said oligomer comprising glycolic acid as said plasticizer.

8. The medical device of claim 1, wherein said biodegradable polymer has a number average molecular weight of 25,000 or more.

9. The medical device of claim 1, wherein the plasticizer comprises said combination of said glycolic acid and said oligomer comprising glycolic acid.

10. The medical device of claim 1, wherein the bioerodable polymeric layer is disposed over the entire substrate.

11. The medical device of claim 1, wherein the bioerodable polymeric layer is disposed over a portion of the substrate.

12. The medical device of claim 1, wherein the medical device is a stent and wherein the biodegradable polymeric layer is disposed over the abluminal surface of the stent, but not the luminal surface.

13. A medical device comprising (a) a substrate; and (b) a bioerodable polymeric layer over the substrate that comprises (i) 50 wt % to 99 wt % of a biodegradable polymer comprising a first monomer, said biodegradable polymer having a number average molecular weight of 10,000 or more, (ii) a therapeutic agent and (iii) 1 wt % to 50 wt % of a plasticizer selected from free first monomer, an oligomer comprising said first monomer, a short polymer comprising said first monomer, a plasticizing polymer that is miscible with said biodegradable polymer, and combinations thereof, wherein the bioerodable polymeric layer has a plasticizer-rich surface, wherein the plasticizer-rich surface is formed by application of a composition containing said plasticizer and said therapeutic agent to the surface of a bioerodable polymeric layer that contains said biodegradable polymer, said plasticizer and said therapeutic agent.

14. The medical device of claim 13, wherein said plasticizer is selected from said free first monomer, said oligomer comprising said first monomer, or a combination thereof.

15. The medical device of claim 13, wherein the plasticizer is said plasticizing polymer that is miscible with the biodegradable polymer.

16. The medical device of claim 13, wherein said medical device is a vascular medical device.

17. The medical device of claim 13, wherein said substrate is a stent.

18. The medical device of claim 13, wherein the therapeutic agent is selected from antithrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

19. The medical device of claim 15, wherein said plasticizing polymer that is miscible with said biodegradable polymer comprises methoxypolyethylene glycol.

20. A medical device comprising (a) a substrate; and (b) a first bioerodible polymeric layer over the substrate that comprises (i) 50 wt % to 99 wt % of poly(lactic acid-co-glycolic acid) as a first biodegradable polymer having a number average molecular weight of 10,000 or more, and (ii) a first therapeutic agent; and (c) a second bioerodible polymeric layer over the first bioerodible polymeric layer that comprises (i) 50 wt % to 99 wt % of poly(lactic-co-glycolic acid) as a second biodearadable polymer, which second biodearadable polymer may be the same as or different from the first biodegradable polymer, said second biodegradable polymer having a number average molecular weight of 10,000 or ore (ii) a second therapeutic agent, which may be the same as or different from the first therapeutic agent, and (iii) 1 wt % to 50 wt % of a plasticizer selected from glycolic acid, an oligomer comprising lactic acid, or an oligomer comprising glycolic acid, wherein said first bioerodible polymeric layer does not contain said plasticizer.

* * * * *